(12) United States Patent
Eberting

(10) Patent No.: US 11,636,947 B2
(45) Date of Patent: *Apr. 25, 2023

(54) SYSTEMS AND METHODS FOR AUTO-GENERATION OF TELEMEDICINE CLINICS

(71) Applicant: Azova, Inc., Alpine, UT (US)

(72) Inventor: Cheryl Lee Eberting, Alpine, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 17/706,144

(22) Filed: Mar. 28, 2022

(65) Prior Publication Data
US 2022/0215941 A1  Jul. 7, 2022

Related U.S. Application Data

(63) Continuation of application No. 16/535,210, filed on Aug. 8, 2019, now Pat. No. 11,289,189, which is a continuation of application No. PCT/US2018/017695, filed on Feb. 9, 2018.

(60) Provisional application No. 62/457,745, filed on Feb. 10, 2017.

(51) Int. Cl.
G16H 40/20     (2018.01)
G16H 80/00     (2018.01)
G06Q 30/0601   (2023.01)

(52) U.S. Cl.
CPC ......... G16H 40/20 (2018.01); G06Q 30/0621 (2013.01); G16H 80/00 (2018.01)

(58) Field of Classification Search
CPC ..... G16H 40/20; G16H 80/00; G06Q 30/0621
(Continued)

(56) References Cited

U.S. PATENT DOCUMENTS 7,912,733 B2 * 3/2011 Clements .............. G16H 80/00
                                                    705/2
11,289,189 B2   3/2022 Eberting
(Continued)

FOREIGN PATENT DOCUMENTS

WO     2012148780 A2    11/2012
WO   WO-2012148780 A2 * 11/2012 ............ G06Q 10/10
WO     2018148594       8/2018

OTHER PUBLICATIONS

Frommer, Telemedicine: The Next Generation Is Here, Jan. 1, 2000, Proceedings Academia/Industry Working Conference on Research Challenges '00. Next Generation Enterprises: Virtual Organizations and Mobile/Pervasive Technologies. AIWORC'00. (Cat. No. PR00628), (pp. 197-203), doi: 10.1109/AIWORC. (Year: 2000).*
(Continued)

Primary Examiner — Joy Chng
(74) Attorney, Agent, or Firm — PCFB, LLC; Justin Flanagan

(57) ABSTRACT

The present disclosure provides systems and methods for automatically generating telemedicine platforms for providers. A marketplace of healthcare services and associated pricing and other terms is made available to employers, individuals, and/or health insurance companies. Employers and/or health insurance companies can select a subset of options from the marketplace to create a customizable sub-marketplace of healthcare services to offer to their employees or insureds. Providers may modify their offerings in the marketplace to fit within guidelines established by the employers or health insurance companies to be automatically included in the sub-marketplace of healthcare services.

29 Claims, 22 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 2008/0275311 | A1* | 11/2008 | Haq | ........................ G06Q 10/10 600/300 |
| 2012/0197660 | A1* | 8/2012 | Prodanovich | .......... G16H 10/40 235/494 |
| 2013/0054678 | A1 | 2/2013 | Williams | |

OTHER PUBLICATIONS

C. E. Koop et al., "Future delivery of health care: Cybercare," in IEEE Engineering in Medicine and Biology Magazine, vol. 27, No. 6, pp. 29-38, Nov.-Dec. 2008, doi: 10.1109/MEMB.2008.929888 (Year: 2008).*

Howard, Are Virtual Care Clinics The Wave Of The Future?, Aug. 17, 2016, U.S. News, https://www.usnews.com/news/articles/2016-08-17/are-virtual-are-clinics-the-wave-of-the-future, pp. 1-8 (Year: 2016).*

PCT/US2018/017695, Written Opinion and International Search Report dated Apr. 27, 2018, 8 pages.

Koop, et al., Future Delivery of Health Care: Cybercare, IEEE Engineering in Medicine and Biology Magazine, vol. 27, No. 6, Nov./Dec. 2008, p. 29-38.

Frommer, Telemedicine: The Next Generation is Here, Telcordia Technologies, Inc., Proceedings Academia/Industry Working Conference on Research Challenges '00, Jan. 1, 2000, pp. 197-203.

Howard, Are Virtual Care Clinics the Wave of the Future?, US News, Aug. 17, 2016, www.usnews.com/news/articles/2016-08-17/are-virtual-care-clinics-the-wave-of-the-future, 8 pp.

Eberting, U.S. Appl. No. 16/535,210, Non-Final Office Action dated Sep. 16, 2021, 15 pp.

* cited by examiner

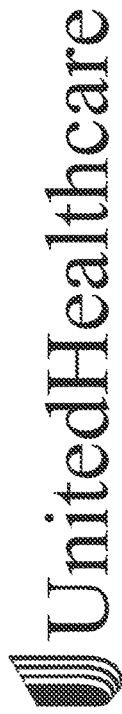
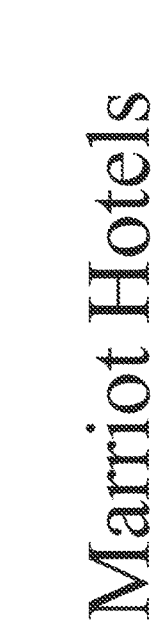
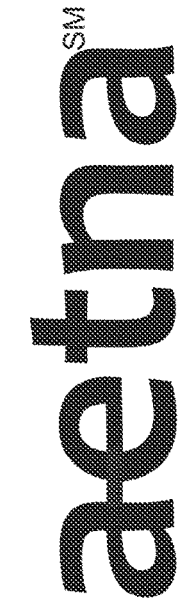
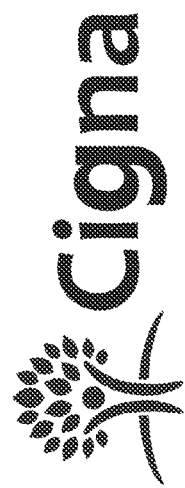
FIG. 2

AZOVA
ALPINE DERMATOLOGY
Face to face video visit with Cheryl Lee Eberting, MD. For patients who have ABC insurance.
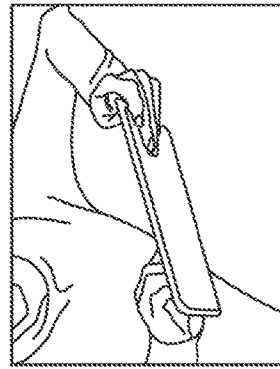
Get treated in Minutes
○ Quick Consult
$29.00/visit
Go
FIG. 4

AZOVA Scheduling: Availability from the provider's HER is displayed when a patient registers for any online visit Availability from provider's HER, pharmacy management system, or radiology information system is displayed to the patient via AZOVA's open APIs.

FIG. 7

Figure 8:
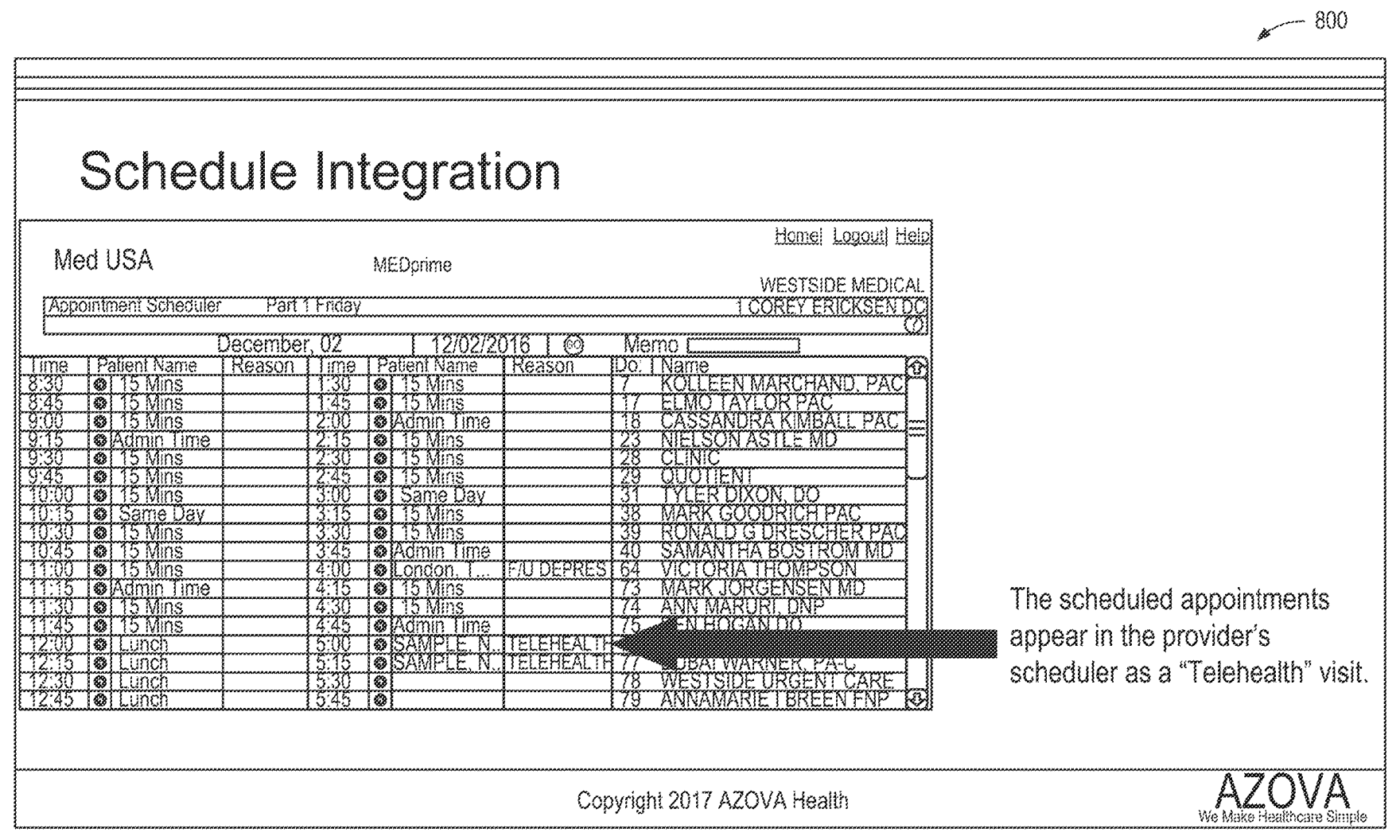

Schedule Integration

Med USA  MEDprime

The scheduled appointments appear in the provider's scheduler as a "Telehealth" visit.

AZOVA

Navigation
- Messages (4)
- Appointments (14) +
- Clinic Setup >
  1. Provider Details
  2. Staff
  3. Additional Providers
  4. Appointment Types
  5. Availability
  6. Provider Groups
  7. Appointment Statuses
  8. Coupons ≡ ✱ | Invite Friends & Family | Invite Health Care Professional | Compose | Address Book | Cheryl Lee Eberling ▾

Provider Details | Education and Licensing

Provider Details

[×]

I am a: [Select / Physician / Nurse Practitioner / Physician Assistant / Mental Health Professional / Health and Wellness Professional / Other Healthcare Professional] ▾    [M.D.] ▾ [×]

NPI # [1306945308]
Example: 1558598797

DEA # [be8718974]
Example: AP5836727

[+ Add More Credentials]

Are you board certified? ●Yes ○No

Do you have a DEA license to prescribe medications? ●Yes ○No

Appointment Types
All Created Appointment Types are tabulated below.

| Current Appointments Types | Archived Appointments Types | Duplicate Appointments Types | | + Add New Membership | + New Appointment Type |

| Title | Price | Action |
|---|---|---|
| Allergy Evaluation: In office visit. 15 minutes | $175.00 | ✎ ● ✕ |
| New Patient In-Office 15 minute | $125.00 | ✎ ○ ✕ |
| In office 15 minutes New Patient | $0.00 | ✎ ● ✕ |
| Live Face to Face Video Visit | $129.00 | ✎ ● ✕ |
| Mole Check Appointment: New Patient 15 minutes | $125.00 | ✎ ○ ✕ |
| Test Video Consultation Visit | $0.00 | ✎ ○ ✕ |
| Photo Forward | $0.00 | ✎ ○ ✕ |
| Quick Question | $19.00 | ✎ ● ✕ |
| Telephone Consultation | $59.00 | ✎ ○ ✕ |
| Ozone IV | $120.00 | ✎ ● ✕ |

FIG. 15

Appointment Types
All Created Appointment Types are tabulated below.

[ + Add New Membership ]  [ + New Appointment Type ]

Current Appointments Types | Archived Appointments Types | Duplicate Appointments Types

| Title | Price | Action |
|---|---|---|
| Allergy Evaluation: In office visit. 15 minutes | $175.00 | ✏️ ● ✖ |
| New Patient In-Office 15 minute | $125.00 | ✏️ ○ ✖ |
| In office 15 minutes New Patient | $0.00 | ✏️ ● ✖ |
| Live Face to Face Video Visit | $129.00 | ✏️ ● ✖ |
| Mole Check Appointment: New Patient 15 minutes | $125.00 | ✏️ ○ ✖ |
| Test Video Consultation Visit | $0.00 | ✏️ ○ ✖ |
| Photo Forward | $0.00 | ✏️ ● ✖ |
| Quick Question | $19.00 | ✏️ ● ✖ |
| Telephone Consultation | $59.00 | ✏️ ● ✖ |
| Ozone IV | $120.00 | ✏️ ● ✖ |

| | | |
|---|---|---|
| Quick Consult For Referrals From Healthcare Professionals | $0.00 | ✏️ ⚫ ❌ |
| Cosmetic Consultation | $0.00 | ✏️ ⚫ ❌ |
| Mole Check Appointment: New Patient 25 minutes | $175.00 | ✏️ ⚫ ❌ |
| PhotoForward(TM) | $49.00 | ✏️ ⚫ ❌ |
| Unlimited Small Area Laser Hair Removal Membership | $0.00 | ✏️ ⚫ ❌ |
| Concierge Clinic | $0.00 | ✏️ ⚫ ❌ |
| $7 Botox + Filler Package | $0.00 | ✏️ ⚫ ❌ |
| Concierge Package #1 Adult 25 years or younger | $0.00 | ✏️ ⚫ ❌ |
| Concierge Package #1 | $0.00 | ✏️ ⚫ ❌ |
| Concierge Single Patient 25-45 years old | $0.00 | ✏️ ⚫ ❌ |
| Concierge Package Adult 18-45 | $0.00 | ✏️ ⚫ ❌ |

FIG. 16B

Change membership fee

Title: Concierge Package Adult 18-45

Description: With this Concierge package you get unlimited in office visits, face to face video consultations and telephone consultations. You can also have two secure messaging visits.

Price Weekly: ○ [-] $ [0.00] [+]

Price Monthly: ○ [-] $ [25.00] [+]

Price Yearly: ○ [-] $ [0.00] [+]

Price Onetime: ○ [-] $ [0.00] [+]

Setup fees (One time): [-] $ [20.00] [+]

FIG. 17A

| | | | |
|---|---|---|---|
| Price Yearly: | - | $ 25.00 | + |
| Price Onetime: | - | $ 0.00 | + |
| Setup fees (One time): | - | $ 0.00 | + |

☐ Continue billing until patient cancel

| | | | | |
|---|---|---|---|---|
| Price Weekly: | ☐ Telephone Consultation | ○ Unlimited | ● Limited Quantity | - 4 + |
| | ☐ Quick Question | ○ Unlimited | ● Limited Quantity | - 2 + |
| | ☐ Urgent Phone Consult | ● Unlimited | ○ Limited Quantity | |
| | ☐ Cosmetic Consultation | ● Unlimited | ○ Limited Quantity | |
| | ☐ New Patient In-Office 15 minute | ○ Unlimited | ● Limited Quantity | - 2 + |

Photo: [ Choose File ]

File size should not be greater than 5MB.

FIG. 17B

SYSTEMS AND METHODS FOR AUTO-GENERATION OF TELEMEDICINE CLINICS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

RELATED APPLICATIONS

This application is a continuation of U.S. patent application Ser. No. 16/535,210 filed on Aug. 8, 2019, titled "SYSTEMS AND METHODS FOR AUTO-GENERATION OF TELEMEDICINE CLINICS," which is a continuation of and claims priority to PCT Patent Application No. PCT/US18/17695 filed on Feb. 9, 2018, titled "Systems and Methods for Auto-Generation of Telemedicine Clinics," which claims priority under 35 U.S.C. § 119 to U.S. Provisional Patent Application No. 62/457,745 filed on Feb. 10, 2017, titled "Systems and Methods for Auto-Generation of Telemedicine Clinics," all of which are hereby incorporated by reference in their entireties, including any appendices thereto.

TECHNICAL FIELD

This disclosure relates to systems and methods for automatic generation of unique telemedicine clinics. Specifically, the systems and methods described herein allow a healthcare provider to automatically generate multiple telemedicine clinics that offer different services, products, and pricing structures.

BRIEF DESCRIPTION OF THE DRAWINGS

Non-limiting and non-exhaustive embodiments of the disclosure are described herein, including various embodiments of the disclosure with reference to the figures listed below.

FIG. 2 provides a graphical illustration of the types of entities for which a unique telemedicine clinic may be created to accommodate each entity's uniquely contracted pricing and approved services, according to various embodiments.

FIG. 4 illustrates a screenshot of a provider's unique telemedicine portal for patients with ABC insurance, according to one embodiment.

FIG. 7 illustrates a screenshot of a provider's unified electronic health record (EHR) combining information from all of the unique telemedicine clinics, according to one embodiment.

FIG. 8 illustrates a screenshot of a provider's schedule integrated with information from all of the provider's unique telemedicine clinics, according to one embodiment.

FIG. 9 illustrates an example portal for initiating a telemedicine consultation, according to one embodiment.

FIG. 12 illustrates a user interface for a provider of any of a wide variety of professional service types to register with the AZOVA™ platform.

FIG. 13 illustrates another embodiment of a user interface for a provider of any of a wide variety of professional service types to register with the AZOVA™ platform.

FIG. 15 illustrates a user interface for customizing and configuring appointment types, according to various embodiments.

FIG. 16A illustrates a user interface with various appointment types, prices, and options for customization, according to one embodiment.

FIG. 16B illustrates an extension of the user interface in FIG. 16A.

FIG. 17A illustrates a user interface for offering a concierge package provider service on the marketplace, according to one embodiment.

FIG. 17B illustrates an extension of the user interface in FIG. 17A, according to one embodiment.

DETAILED DESCRIPTION

Figure 1A:
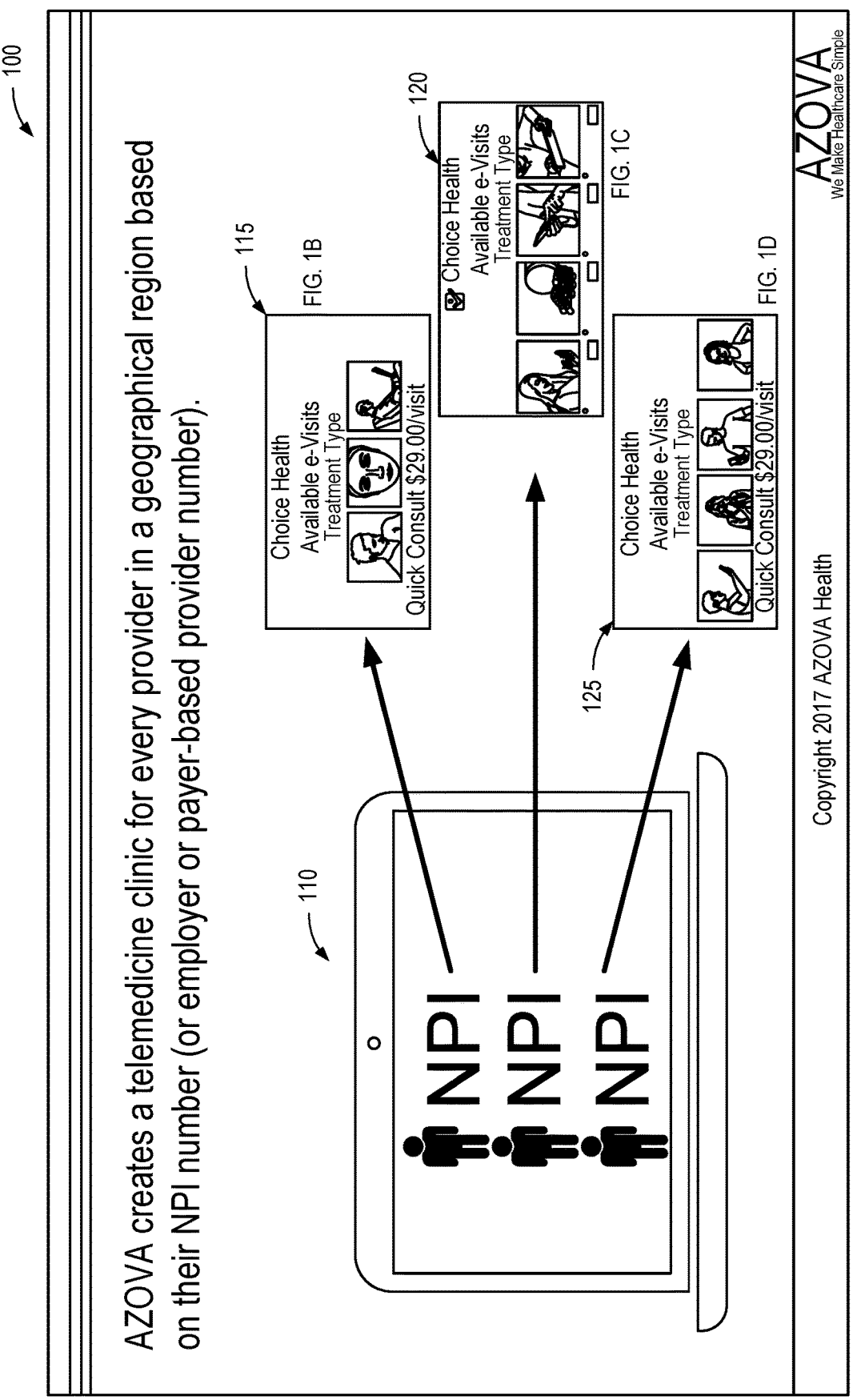
FIG. 1A illustrates a block diagram of three telemedicine clinics being generated that correspond to three national provider identifier (NPI) numbers, according to one embodiment.

This disclosure provides systems and methods for automatically generating telemedicine clinics that are customized based on applicable provider(s) and payer(s). Details and examples are provided with reference to the figures below. Various embodiments of this disclosure can be incorporated into, used by, and/or used in conjunction with one or more of the embodiments or combination of embodiments described in U.S. patent application Ser. No. 15/597,102 titled "Telemedicine Platform with Integrated e-Commerce and Third Party Interfaces," filed on May 16, 2017 (the "'102 application" and/or PCT Application No. PCT/US2016/020964 titled "Telemedicine Platform and Associated Services with Third-Party Interfaces," filed on Mar. 4, 2016, both of which are hereby incorporated by reference in their entireties. Similarly, the infrastructure and underlying principles described the incorporated applications can be used to implement and/or augment the systems and methods described herein.

Individuals seeking healthcare may attempt to obtain healthcare directly from a provider, such as a family practitioner, pediatrician, dermatologist, gastrointestinal physician, gynecologist, dentist, orthodontist, ophthalmologist, etc. Providers may be individual providers, or providers that are part of a healthcare facility, such as multi-practitioner office, a hospital, an urgent care facility, or the like.

Rather than seek out an individual provider, individuals may participate in a group health insurance plan. Group health insurance plans may provide fixed prices, discounted services, deductible-based services, copay-based services and/or the like to a group of individuals seeking healthcare. The group health insurance entity may contract with specific providers to the exclusion of others. The contracted providers may agree to discounted rates and/or fee caps in exchange for payment and workflow assurances from the group health insurance entity.

Providers have an interest in offering telehealth consultations and other telemedicine offerings, such as those described in the '102 application. However, individual providers and even groups of providers (e.g., a doctor's office, hospital, consortium of providers, etc.) may not have the technical expertise to operate the hardware and software necessary to operate a telemedicine platform. Moreover, health insurance companies and/or employers may desire some level of uniformity in telemedicine offerings among tens, hundreds, or even thousands of providers within their network.

In some circumstances, individuals seeking healthcare may obtain healthcare benefits from an employer. The employer may directly contract with healthcare providers for discounted services and directly pay all or a portion of their employees' healthcare costs. In other embodiments, the employer may contract with a group health insurance entity to provide the employer's employees with healthcare coverage of one form or another.

Healthcare practitioners may contract with multiple employers and/or group health insurance entities and/or sub-programs thereof. As a specific illustration, a group of five healthcare practitioners may be part of an urgent care clinic. The urgent care clinic may agree to a first fee schedule with a first health insurance company and a second fee schedule with different terms with a second health insurance company. A dermatologist may contract with the second health insurance company only.

A first employer may contract with the first health insurance company to provide its employees with healthcare through the urgent care clinic, but its employees could not utilize the dermatologist's services through their employer-provided healthcare coverage. A second employer may contract with the second health insurance company, and its employees could utilize the services of both the urgent care clinic and the dermatologist at the agreed-upon rates in the second fee schedule.

The urgent care clinic may have different rates and rules in the first fee schedule with the first health insurance company than it does with the second fee schedule with the second health insurance company. The urgent care clinic may have different fee schedules with dozens of insurance companies. One or more companies (e.g., non-insurance related business entities) may also directly negotiate a fee schedule with the urgent care clinic. The variations in terms, rates, and rules further complicates the situation and makes it very difficult for the urgent care clinic to operate a single telemedicine platform.

Moreover, no single health insurance company can develop a workable telemedicine platform for all of the providers within its network, because any such telemedicine platform would not adequately meet the needs of providers that have patients covered by other health insurance companies that pay different rates and reimburse a different subset of healthcare services. As a specific example, a provider may accept patients that are covered by a first insurance company. That first insurance company may pay the provider for a first set of services according to a first fee schedule. The provider may also accept Medicaid patients, Medicare patients, uninsured (cash-paying) patients, and patients from a second insurance company—each of which may allow for reimbursement of different services at different rates. A telemedicine platform offered by the first insurance company is not sufficiently comprehensive for the provider.

Accordingly, the industry has failed to provide a universally workable telemedicine platform except for in the rare instances in which providers contract exclusively with a single health insurance company, or no health insurance company at all. Such an arrangement detrimentally reduces the provider's freedom to offer services to a wide variety of patients, and reduces competition between providers to the detriment of patients.

The presently described systems and methods provide an electronic marketplace for providers to offer telemedicine services to patients, health insurance companies, and/or employers through a unifying telemedicine platform that provides a single provider portal connected to dozens of distinct telemedicine clinics—each of which may be uniquely branded, associated with unique URLs, and offer differing services according to differing price schedules. Additional functionalities and the underlying infrastructure of the telemedicine platform are described in detail in the '102 application.

In some embodiments, providers may offer telemedicine services only to health insurance companies and/or employers, and not directly to patients. In other embodiments, providers may offer services only to patients directly, only to customers of health insurance companies, or only to employees through an employer.

Providers (individually or through a multi-provider practice such as a hospital) may create (or claim and customize as described below) an online clinic via the AZOVA™ platform. Each healthcare provider or group of providers may customize the offerings, prices, availability etc. as they see fit. The healthcare providers may establish their own rates, rules, discounts, etc. and determine which types of services will be available via telemedicine sessions on a telemedicine platform, and which types of services may be scheduled on the platform but require in-person visits. Accordingly, the system facilitates the creation of a marketplace of offerings from hundreds or thousands of providers with a wide variety of specialties and price points. The providers may offer different prices for individual care and group-rate care.

In some embodiments, an individual may browse the marketplace and select a desired service, schedule a telemedicine consultation, and/or conduct the telemedicine consultation via the telemedicine platform. The patient may pay the provider directly, receive a bill, or pay via the telemedicine platform. In some embodiments, the telemedicine platform may guarantee payment to the provider. In other embodiments, the telemedicine platform may simply facilitate the marketplace exchange and enable the telemedicine consultation, leaving the provider responsible for collecting or receiving payment.

In other embodiments, a health insurance company may evaluate the provider offerings in the marketplace and select a subset of the offerings to generate a sub-marketplace. For example, the health insurance company may select a subset of the offerings from providers that agree to provide group discounts, or are under a defined fee cap for specific services, and/or provide a desired breadth of services within threshold price ranges. The health insurance company may then market the sub-marketplace of approved providers and offerings to its customers.

Similarly, an employer may desire to pay for all or a portion of its employees' healthcare costs. In various embodiments, the telemedicine platform may evaluate the claims history of the employees of the employer to determine the number, location, and types of healthcare practitioners needed. The telemedicine platform may then evaluate the marketplace (or allow the employer to manually evaluate the marketplace) to identify suitable providers within a target price range. The employer may select a subset of the offerings in the general marketplace to create a sub-marketplace of provider services that it can offer to its employees.

From an employee's perspective, her employer may appear to have a telemedicine platform that allows her to select from a subset of providers offering various services, some of which can be provided via a telemedicine consultation. The employee may have various options that are all free or subject to differing copays or deductibles. The employee may be able to select from multiple providers for a particular service, or only a single provider (i.e., individual provider or group of providers in a specific office or hospital) for each of a wide variety of services. In some embodiments, the employee may be able to select providers outside of the employer's specific subset of providers services for an additional fee or without any financial help from the employer. In other embodiments, the telemedicine platform may limit the employee's options to those explicitly selected as part of the employer's subset of offerings.

In some embodiments, an employee of an employer or a customer of a healthcare company may be able to search an online directly of services available to them and sort and filter them as desired. For example, the entire marketplace may include 5,000 healthcare providers. The healthcare company may have selected only 1,100 of those 5,000 for inclusion in their sub-marketplace. An employer may contract with the healthcare company to provide healthcare coverage to its employees. The employees become customers of the healthcare company. From an individual customer's perspective, he or she is able to search a customized portal branded or co-branded for the healthcare company and/or the employer of the customer. The customized portal with the sub-marketplace of offerings may allow for searching and filtering of the 1,100 providers in the sub-marketplace. Once the customer identifies a desired service, the customer may initiate a real-time telemedicine consultation or schedule a future telemedicine or in-person consultation.

From the employer's perspective, the employer can offer its employees a custom suite of healthcare services at fee schedules and other terms that it selects and/or approves. The employer can use the marketplace provided by the telemedicine platform to negotiate rates and service terms directly with healthcare providers instead of through a health insurance company. In some embodiments, the employer can appear to offer telemedicine consultations to its employees through the telemedicine platform (e.g., a skinned version or portal of the AZOVA™ platform customized for the specific employer). The employer may restrict the availability of some, more expensive, healthcare provider specialists until recommendations are received from less expensive general healthcare providers.

In one embodiment, the system analyzes the historical claims of the employees of an employer. The system then recommends a subset of the services available on the marketplace to meet the specific needs of the employees based on the historical claims. The system then provides an employer-branded portal accessible to the employer's employees that allows them to schedule telemedicine consultations and/or in-person consultations with the recommended subset of providers. Various financial arrangements are possible between the providers, the telemedicine platform, the employer, and the employees that may include monthly premiums, negotiated group discounts, deductibles, copayments, capitated payment schedules, guaranteed minimum payments, on-call fees, commissions, payment processing fees, brokerage fees, etc.

From an insurance company's perspective, providers are available for inclusion in their provider network with little or no transaction cost with uniform telemedicine service offerings. Some employers and/or individuals may decide to obtain health insurance through a health insurance company under a traditional model. Traditionally, the health insurance company has one or more provider networks that it offers to its customers (employers or individuals). The health insurance company typically negotiates discounted rates, fee schedules, availability, service guarantees, etc. with each provider in each of its provider networks. The systems and methods described herein allow the health insurance company to browse the marketplace of healthcare offerings from various provides and select them for inclusion within a specific provider network. The telemedicine platform enables the health insurance company to create a branded sub-marketplace of provider offerings that it can share with its insured. Telemedicine consultations, in-person consultation scheduling, translations services, secure messaging, and various other features may be offered by the health insurance company to its insured via the telemedicine platform.

From the healthcare provider's perspective, the telemedicine platform provides customized and distinct online clinics for each of his or her patients, regardless of who the patient's employer is or who insures the patient (i.e., the payer). A provider may effectively have hundreds of distinct online clinics—one for each insurance company and employer with whom he or she is affiliated. For example, the healthcare provider may have a first online clinic with various services, prices, rules, etc. for a small business with 30 employees. The same healthcare provider may offer steep discounts and a limited number of services to customers of a particular health insurance company. Accordingly, healthcare provider may have a distinct online clinic accessible to customers of that particular health insurance company. The healthcare provider may partner with multiple employers, health insurance companies, and/or provider networks within a single health insurance company, each of which may be facilitated by a distinct online clinic.

However, the telemedicine platform may provide a unifying scheduling platform and a unifying access portal for the healthcare provider. Thus, while each patient may see a different subset of offerings, prices and availability, the healthcare provider is able to agnostically tend to each patient through a single access portal and view scheduled telemedicine and in-person consultations in a single calendar. The unifying provider interface greatly simplifies the experience for the healthcare provider.

In some embodiments, a healthcare provider may view standard or acceptable rates set by employers and/or health insurance companies when determining what rates and services they would like to add to the marketplace of provider services. In some embodiments, a hospital with multiple providers with various specialties may add various services to the marketplace at various prices without necessarily associating each service with an individual provider. The hospital may choose to set the rates and terms of each service to fit within predefined guidelines set by an insurance company or employer so that they can be automatically (or at least considered) for inclusion in the sub-marketplace of the insurance company or employer.

Similarly, a single provider may decide to set his or her rates to fit within guidelines that will enable him or her to be included in the sub-marketplace of a specific employer and/or health insurance company. In some embodiments, a provider or group of providers may submit varying terms for various services depending on the size of the employer or health insurance company. For instance, a provider may be willing to offer substantial discounts to be part of the sub-marketplace offered by an employer of 3000 employees, but charge higher prices for a small business with only 10 employees based, for example, on the uncertainty of getting paid by the small business.

Another benefit for healthcare providers and/or their patients may be the ability for provider-to-provider consultations supported and paid for by the patient, employer, or health insurance company. For example, a patient may initiate a telemedicine consultation with a general practice family doctor. The patient may be having negative symptoms with a particular antidepressant medication. Rather than refer the patient to a specialist, which might require the patient to relay extensive amounts of redundant information to the specialist in order for the specialist to make an informed recommendation, the family doctor may initiate a separate provider-to-provider consultation. The family doctor may quickly obtain a recommendation from the specialist. The telemedicine platform described herein allows for both the family doctor and the specialist to charge an appropriate fee for their services, thereby encouraging the most efficient treatment of patients.

In such a model, a neuro-specialist may offer only provider-to-provider services as part of a sub-marketplace of a particular employer. The neuro-specialist may agree to be on call for provider-to-provider neurological questions in exchange for a flat monthly fee. The neuro-specialist may refuse to directly interact with patients and/or offer other services and varying prices and other terms for patient-to-provider services.

The market place may be bi-directional in that, in addition to allowing providers to offer services and associated prices, consumers (e.g., individual patients, employers, health insurance companies, etc.) may be able to list the prices they are willing to pay for specific services. These consumers may provide various details such as the types of services they want or demand, the number individual patients in their group, payment terms, guarantees, on-call fee arrangements, etc. Providers may evaluate these offerings and agree to join provider networks (sub-marketplaces) that offer acceptable terms.

A provider who becomes part of a sub-marketplace for multiple employers and health insurance companies may have a single dashboard or portal to interact with all of the patients, even though each of those patients may be using a different online clinic and see different pricing and service options. For example, a first employer may agree to pay $45 for a 15-minute telemedicine consultation, while a second employer may agree to pay $60 for a 30-minute telemedicine consultation. The systems and methods described herein allow for a single provider to access a single dashboard or portal that is associated with tens or even hundreds of distinct telemedicine clinics with varying prices and service options.

The following example illustrates one possible workflow enabled by the systems and methods described herein. The system may provide 700 healthcare providers with a telemedicine clinic dashboard that allows them to conduct telemedicine consultations, schedule appoints, share secure messages and images, submit prescriptions to pharmacists, collaborate with other providers, and/or access any of the other features of the telemedicine platform described in the '102 application. Each of these 700 healthcare providers submits the healthcare services they offer and associated terms (e.g., fees, discounts, billing rules, etc.). For instance, a dermatologist may offer 30-minute acne analysis via a telemedicine consultation for $125. A first pediatrician may offer a 20-minute general telemedicine consultation for $95. A second pediatrician may offer a 45-minute general telemedicine consultation for $185.

An employer may request a customized telemedicine platform portal and sub-marketplace of services and providers for its 5,000 employees. The employer may manually select which of the 700 healthcare providers it would like to include in its sub-marketplace that it makes available to its employees. Alternatively, a general analysis of claims for 5,000 people, or a specific analysis of the historical claims of the 5,000 employees of the specific employer, may be used to determine the types of services needed. A subset of the 700 providers may be selected to meet the needs of the employees based on the pricing and other terms the employer is willing to pay for.

For example, an analysis of the historical claims may review that the employees have used 580 of the 700 providers available in the marketplace, but 217 of those providers have relatively low ratings and 35 of those providers are priced higher than the employer's thresholds. Accordingly, the system may automatically generate a sub-marketplace for the employer to offer its employees via a customized portal that includes 328 providers (580−217−35=328).

Optionally, the system may determine that the employer's thresholds do not allow for any cardiac surgeons and recommend that a cardiac surgeon be added to the sub-marketplace based on the expected healthcare needs of the employees even though the pricing terms may be outside of the employer's established thresholds. Optionally, some providers may be notified that they were not included within the newly created sub-marketplace because the services they offer and/or the terms of those services did not fit within the established guidelines of the employer. Some providers may decide to modify their offerings in the marketplace to conform to the employer's guidelines. In some embodiments, the provider may be automatically added to the sub-marketplace based on conformance. In other embodiments, the employer may be notified that the provider now conforms to the guidelines any may or may not elect to add them to the sub-marketplace.

In one embodiment, the entire marketplace of offerings from healthcare providers is available to all users of the platform with default pricing and other terms. Employers and/or health insurance companies negotiate, through the telemedicine platform, with the providers to provide varying discounts and/or other special terms of service. For example, a large employer may negotiate a 17% discount off retail price that is applied to the fees charged by any provider that is part of the network for services provided to an employee of that large employer.

Some of the infrastructure that can be used with embodiments disclosed herein is already available, such as: general-purpose computers, computer programming tools and techniques, digital storage media, and communications networks. A computer may include a processor, such as a microprocessor, microcontroller, logic circuitry, or the like. The processor may include a special-purpose processing device, such as an ASIC, a PAL, a PLA, a PLD, a CPLD, a Field Programmable Gate Array (FPGA), or other customized or programmable device. The computer may also include a computer-readable storage device, such as non-volatile memory, static RAM, dynamic RAM, ROM, CD-ROM, disk, tape, magnetic, optical, flash memory, or other computer-readable storage medium.

Suitable networks for configuration and/or use, as described herein, include any of a wide variety of network infrastructures. Specifically, a network may incorporate landlines, wireless communication, optical connections, various modulators, demodulators, small form-factor pluggable (SFP) transceivers, routers, hubs, switches, and/or other networking equipment.

The network may include communications or networking software, such as software available from Novell, Microsoft, Artisoft, and other vendors, and may operate using TCP/IP, SPX, IPX, SONET, and other protocols over twisted pair, coaxial, or optical fiber cables; telephone lines; satellites; microwave relays; modulated AC power lines; physical media transfer; wireless radio links; and/or other data transmission "wires." The network may encompass smaller networks and/or be connectable to other networks through a gateway or similar mechanism.

Aspects of certain embodiments described herein may be implemented as software modules or components. As used herein, a software module or component may include any type of computer instruction or computer-executable code located within or on a computer-readable storage medium, such as a non-transitory computer-readable medium. A software module may, for instance, comprise one or more physical or logical blocks of computer instructions, which may be organized as a routine, program, object, component, data structure, etc., that perform one or more tasks or implement particular data types, algorithms, and/or methods.

A particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network. In a distributed computing environment, software modules may be located in local and/or remote computer-readable storage media. In addition, data being tied or rendered together in a database record may be resident in the same computer-readable storage medium, or across several computer-readable storage media, and may be linked together in fields of a record in a database across a network.

The various functional components of the described systems and methods may be modeled as a functional block diagram that includes one or more remote terminals, networks, servers, data exchanges, and software/hardware/firmware modules configured to implement the various functions, features, methods, and concepts described herein. In many instances, each application, embodiment, variation, option, service, and/or other component of the systems and methods described herein may be implemented as a module of a larger system. Each module may be implemented as hardware, software, and/or firmware, as would be understood by one of skill in the art for the particular functionality, and may be part of a larger physical system that may include computer-readable instructions, processors, servers, endpoint computers, and/or the like.

The embodiments of the disclosure can be understood by reference to the drawings, wherein like parts are designated by like numerals throughout. The components of the disclosed embodiments, as generally described and illustrated in the figures herein, could be arranged and designed in a wide variety of different configurations. Further, those of skill in the art will recognize that one or more of the specific details may be omitted, or other methods, components, or materials may be used. In some cases, operations are not shown or described in detail. Thus, the following detailed description of the embodiments of the systems and methods of the disclosure is not intended to limit the scope of the disclosure, as claimed, but is merely representative of possible embodiments.

FIG. 1A illustrates a block diagram 100 of three telemedicine clinics (115, 120, and 125) being generated that corresponding to three national provider identifier (NPI) numbers 110, according to one embodiment. A telemedicine platform or stand-alone system may include an automatic telemedicine clinic generation (ATCG) system configured to identify one or more providers. An ATCG system may, for example, be embodied as a server implementing computer instructions. Example approaches for identifying each provider include using a national provider identification (NPI) number, and employer number, a tax identification number, a social security number, or the other unique identifier.

The ATCG system may automatically generate a telemedicine clinic on demand, for each provider associated with a specific insurance company or employer (or other payer), for each provider associated with a specific healthcare facility, for each provider associated with a specific employer, or for every provider within a specific geographic or politically-defined region. For example, in one embodiment an ATCG system may create a telemedicine clinic for every provider in the United States or some other geographic or politically defined region based on NPI number.

The ATCG system may generate a plurality of telemedicine clinics for each provider with default configuration settings that may be subsequently customized by the provider. For each provider, a telemedicine clinic may be automatically generated for each insurance company or employer (or other payer, such as a union, consortium, club, etc.) associated with the ATCG system. In some embodiments, the system may generate a telemedicine clinic on behalf of a provider for each insurance company or employer associated with the provider.

In some embodiments, the system may generate a telemedicine clinic on behalf of a provider for each insurance company or employer associated with a geographic region relevant to the provider. In some embodiments, the system may generate a telemedicine clinic on behalf of a provider for each insurance company or employer known to support some form of telemedicine. For example, for a provider practicing in Chicago, Ill., the ATCG system may be configured to auto-populate, auto-generate, and/or generate on demand a distinct telemedicine clinic for one or more locally available health insurance companies and one or more large employers in the area that may not use a traditional health insurance company to provide healthcare to their employees.

Specifically illustrated in FIG. 1A, a customizable telemedicine clinic is generated for each of three providers (115, 120, and 125) based on their NPIs 110 for a single health insurance company (Choice Health). The system populates each provider's telemedicine clinic (115, 120, and 125) with the provider's unique offerings and with pricing terms for Choice Health (that may be subsequently customized).

Figure 1B:
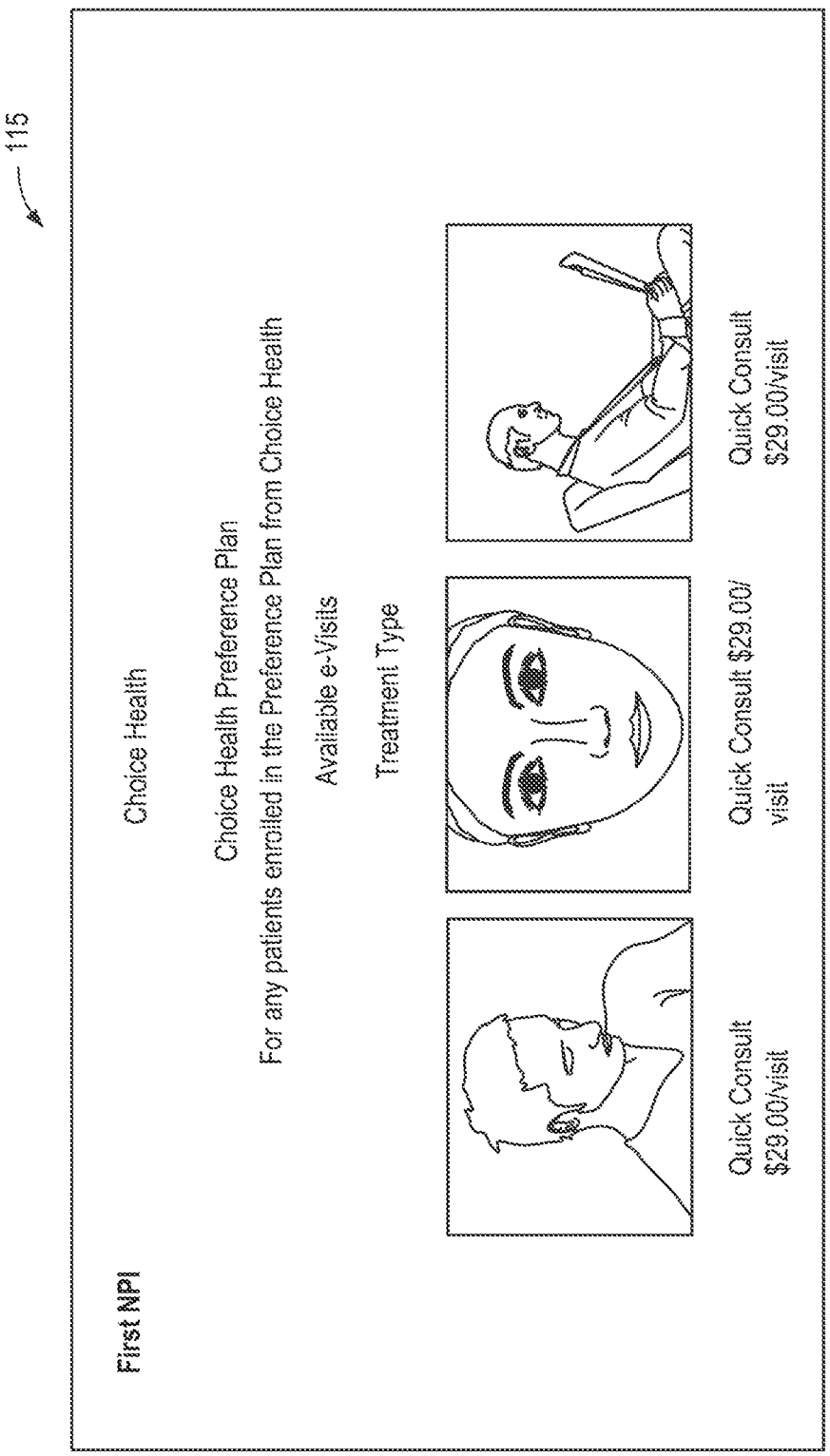
FIG. 1B illustrates services offered by the provider associated with the first NPI number for a particular healthcare plan.

FIG. 1B illustrates a simplified display 115 of the services offered by the provider associated with the first NPI number in FIG. 1A for the Choice Health insurance company. As illustrated, the first provider may offer three types of "quick consult" visits for $29 each.

Figure 1C:
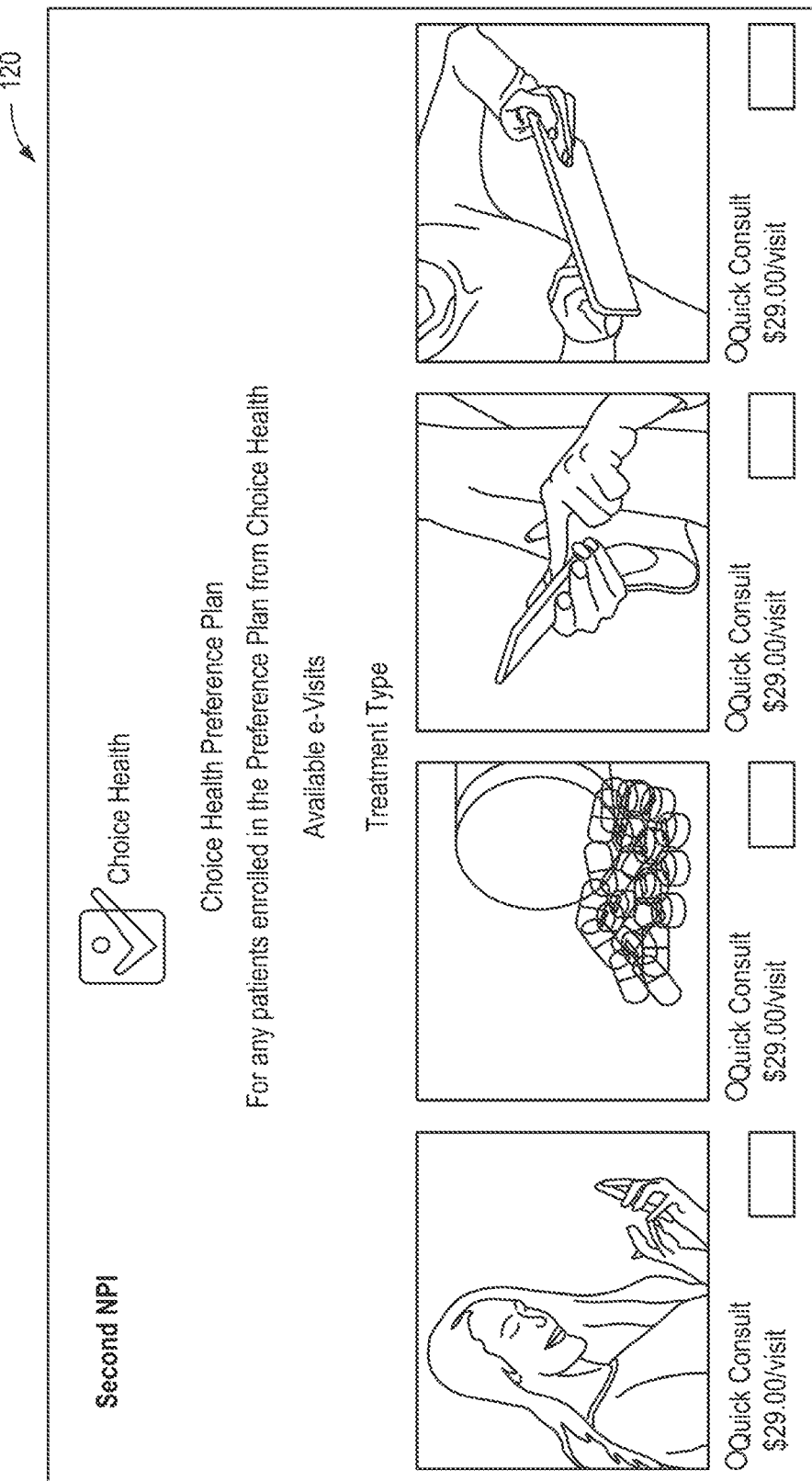
FIG. 1C illustrates services offered by the provider associated with the second NPI number for the particular healthcare plan.

FIG. 1C illustrates a simplified display 120 of the services offered by the provider associated with the second NPI number in FIG. 1A for the Choice Health insurance company. As illustrated, the second provider may offer four types of "quick consult" visits for $29 each.

Figure 1D:
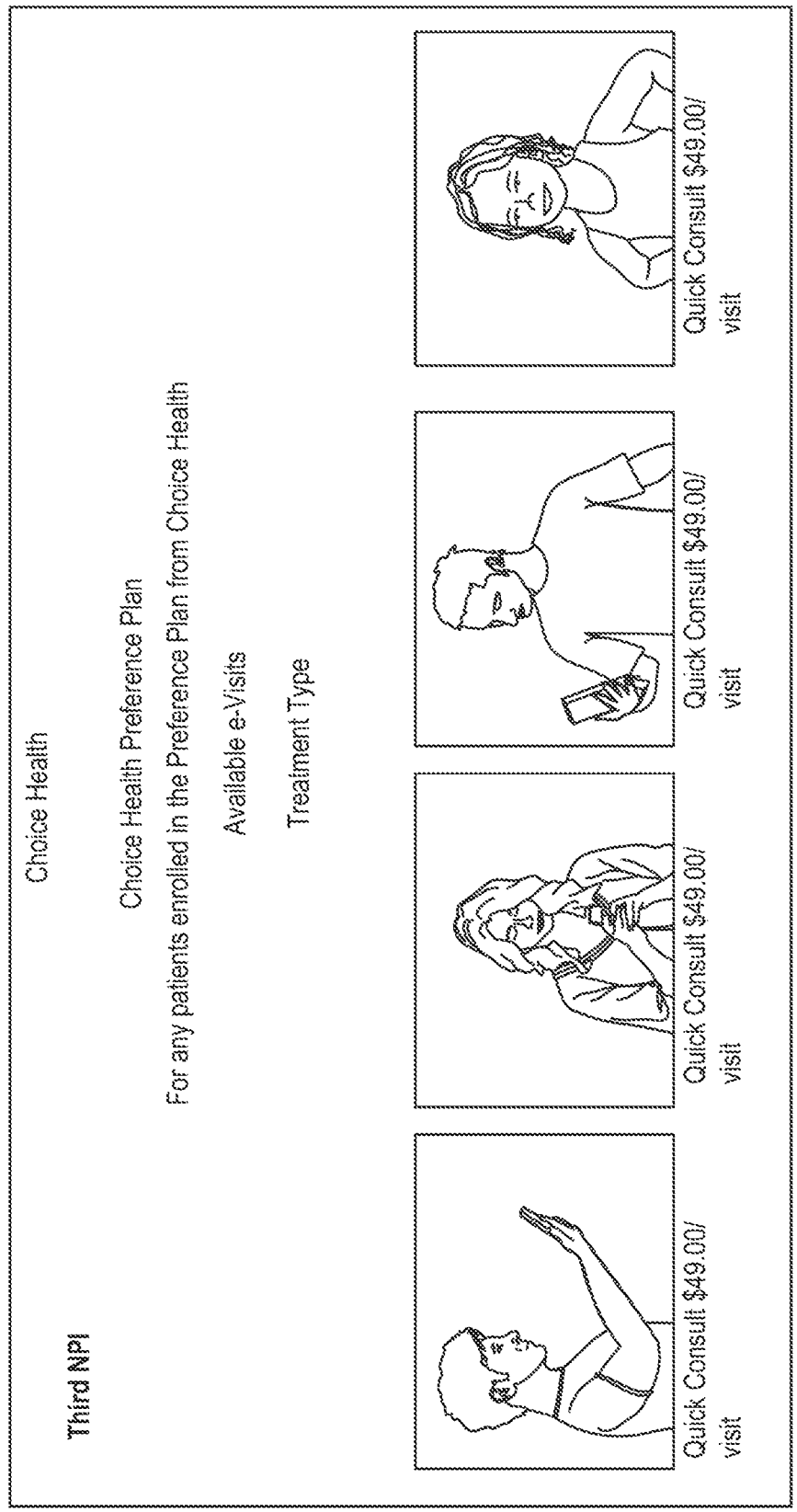
FIG. 1D illustrates services offered by the provider associated with the third NPI number for the particular healthcare plan.

FIG. 1D illustrates a simplified display 125 of the services offered by the provider associated with the third NPI number in FIG. 1A for the Choice Health insurance company. As illustrated, the third provider may offer four types of "quick consult" visits for $49 each. For instance, the third provider may be a specialist and therefor offer unique services at an elevated price.

FIG. 2 provides a graphical illustration 200 of the types of entities for which a unique telemedicine clinic may be created. In various embodiment, they system may generate a unique telemedicine clinic on behalf of a provider for each of the various entities. In FIG. 2, example entities for which telemedicine clinics could be generated are shown as Blue-Cross BlueShield, Cigna, UnitedHealthcare, Marriot Hotels, and Aetna. Each of these is merely an example and no affiliation, ownership or rights to the trademarks is implied or suggested by this application. Specifically, the respective tradenames and service marks in FIG. 2 are owned by the respective companies and are not necessarily affiliated with the Azova™ platform.

In some embodiments, the system generates unique telemedicine clinics on behalf of a provider to accommodate each entity's uniquely contracted pricing and approved services. According to various embodiments, the ATCG system may include a database with contracted pricing and available (e.g., reimbursable) services offered by one or more payers (e.g., insurers, patients themselves, health savings account managers, insurance companies, employers, unions, corporations, non-profit entities, charities, hospitals, etc.).

A payer may be anybody who is obligated to and/or may for some other reason reimburse or directly pay for the healthcare costs of a patient—including the patient themselves. A provider is frequently described herein as being a single healthcare practitioner or service provider; however, it is appreciated that in each instance in which the term "provider" is used, the term "provider" may be a group of providers, such as doctor's office or hospital.

Figure 3:
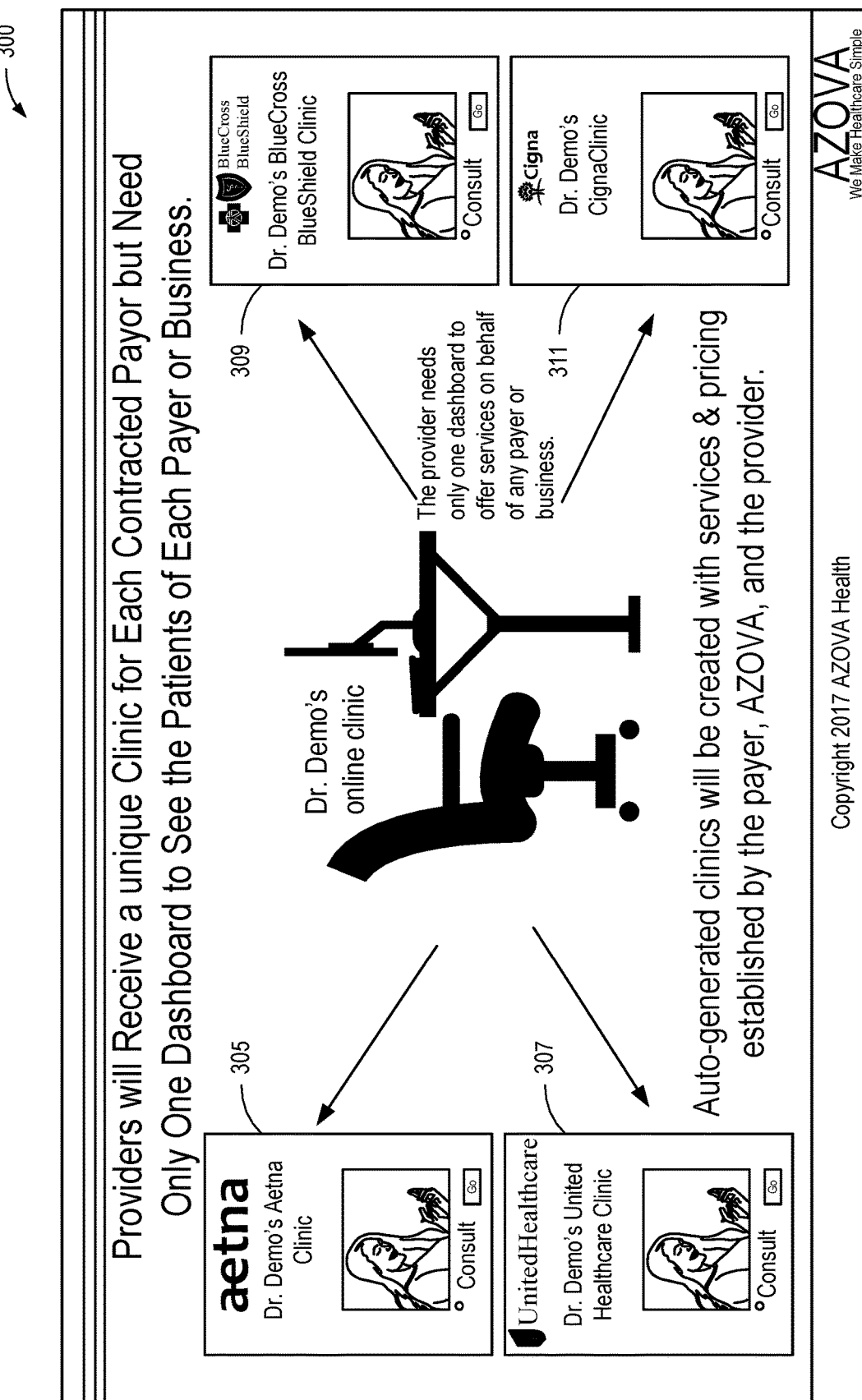
FIG. 3 illustrates a graphical representation of a provider associated with four auto-generated telemedicine clinics, according to one embodiment.

FIG. 3 illustrates a graphical representation 200 of a provider (Dr. Demo) associated with four auto-generated telemedicine clinics 305, 307, 309, and 311. Each company, such as an insurance company or another employer, may have different contracted rates, premiums, deductibles, or co-pays for various telemedicine services offered by Dr. Demo. As previously noted, the examples of Aetna, United Healthcare, BlueCross BlueShield, and Cigna are used in the illustrations throughout but are not necessarily affiliated with the Azova™ platform and the ownership of each of these marks is reserved by the respective companies.

Some insurance companies may not reimburse certain types of activities when done via telemedicine. Accordingly, the ATCG system may create unique telemedicine clinics 305, 307, 309, and 311 for each contracted payer. However, in various embodiments, the provider (Dr. Demo) may see them all through a unified portal and integrate all of the information from each of the individual telemedicine clinics into unified EHR systems, billing systems, scheduling system, etc. The ATCG system may integrate with any EHR so providers can offer telehealth services to patients from any payer or business at a contracted rate with a seamless workflow using all of their existing EHR.

Thus, from the perspective of Dr. Demo, he runs a single clinic and agnostically treats patients regardless of who the ultimate payer may be. From the perspective of the patient, they see a telemedicine portal and offered services that are covered by their insurance company and that are available to them at contracted prices. From the perspective of the insurance company, the healthcare provider has a telemedicine portal customized to their approved services and contracted rates.

An integrated, unified or connected billing, scheduling, and/or EHR system may facilitate a unified approach from Dr. Demo's vantage point, but uniquely bill each insurance company or employer based on contracted rates. While Dr. Demo may see a scheduled telemedicine session on a calendar, selecting the session may automatically launch the correct telemedicine clinic 305, 307, 309, and 311 and connect him to the patient.

The ATCG system may charge each provider, insurance company, other payer, facility, and/or patient a one-time fee, a monthly fee, or a usage-based fee. Other fee and billing arrangements are contemplated as are known in the art for sales of products, services, and software-as-a-service.

FIG. 4 illustrates a simplified screenshot 400 of a provider's unique telemedicine portal for patients with ABC insurance, according to one embodiment. As illustrated, a unique uniform resource locator (URL) address may be auto-generated and registered with ICANN through a domain name registrar for each provider's online clinic, for each payer, and/or for each employer. The actual implementation of the telemedicine services and products may be implemented through the provider's EHR or a telemedicine platform, like the Azova™ platform and/or as detailed in the '102 application.

Figure 5:
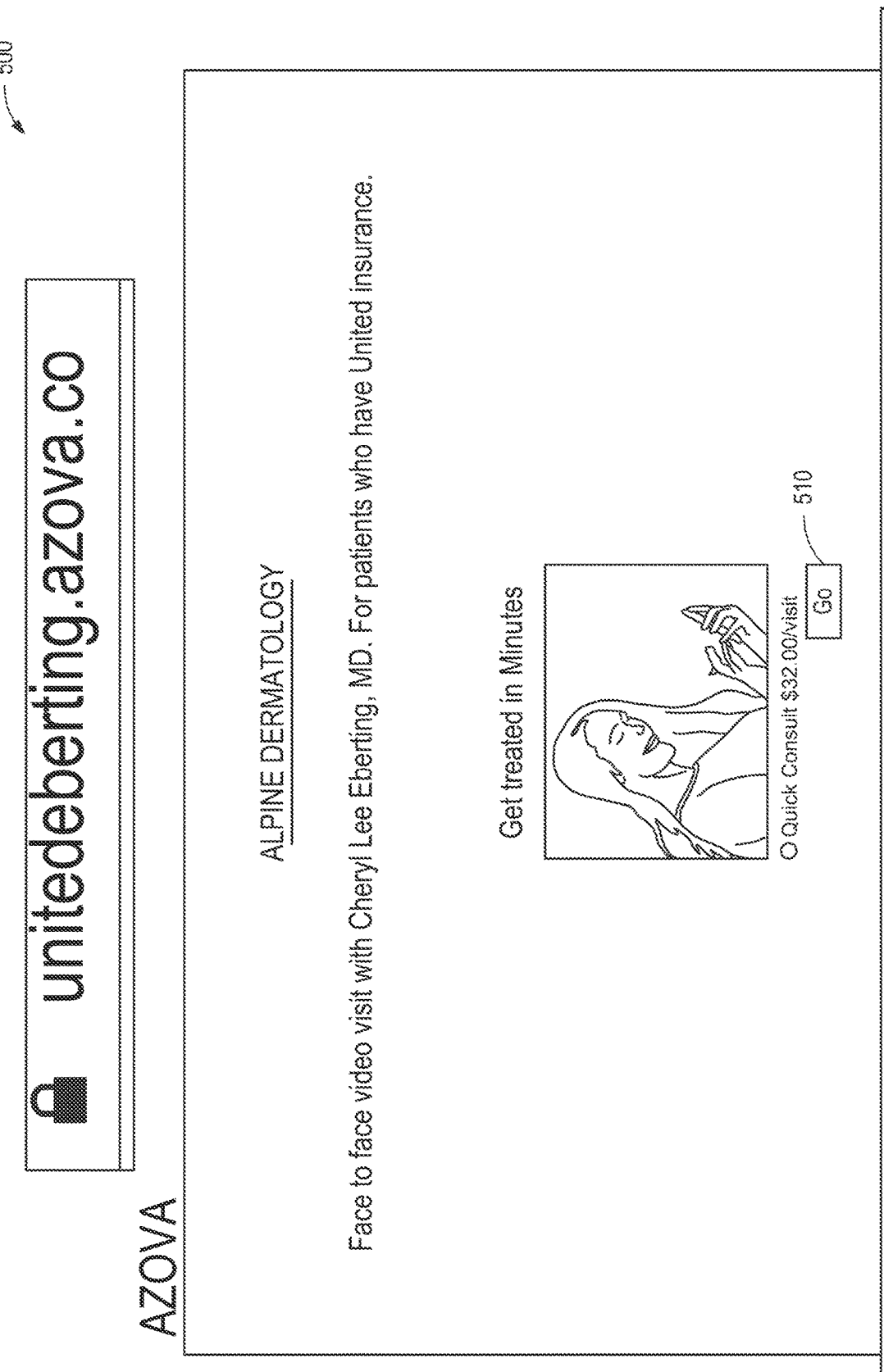
FIG. 5 illustrates a screenshot of the same provider's unique telemedicine portal for patients with United insurance, according to one embodiment.

FIG. 5 illustrates a simplified screenshot 500 of the same provider's unique telemedicine portal for patients with United insurance, according to one embodiment. As illustrated, the same provider may have another unique URL associated with a different insurance company. A patient accessing the URL may select the quick consult by clicking on the "Go" button 510 to instantly launch a telemedicine consultation with Dr. Eberting. In other embodiments, the "Go" button 510 may direct the patient to a scheduling interface to schedule an appointment with Dr. Eberting. As previously described Dr. Eberting may have tens or even hundreds of unique URLs and/or telemedicine clinics. However, on the backend, each of these telemedicine clinics is associated with a single unified portal for the provider.

Each of the portals (FIG. 4 for ABC and FIG. 5 for United Healthcare) may be customized based on the services that the insurance company approves, supports, and/or covers and/or for which they have different contracted rates. Thus, in the illustrated embodiments, a "Quick Consult" may involve different services or the same services at different prices. In some embodiments, no price may be shown because the services may be covered completely by the payer. In other embodiments, the price shown may be associated with the deductible, copay, or co-insurance that the patient will be required to pay.

Figure 6:
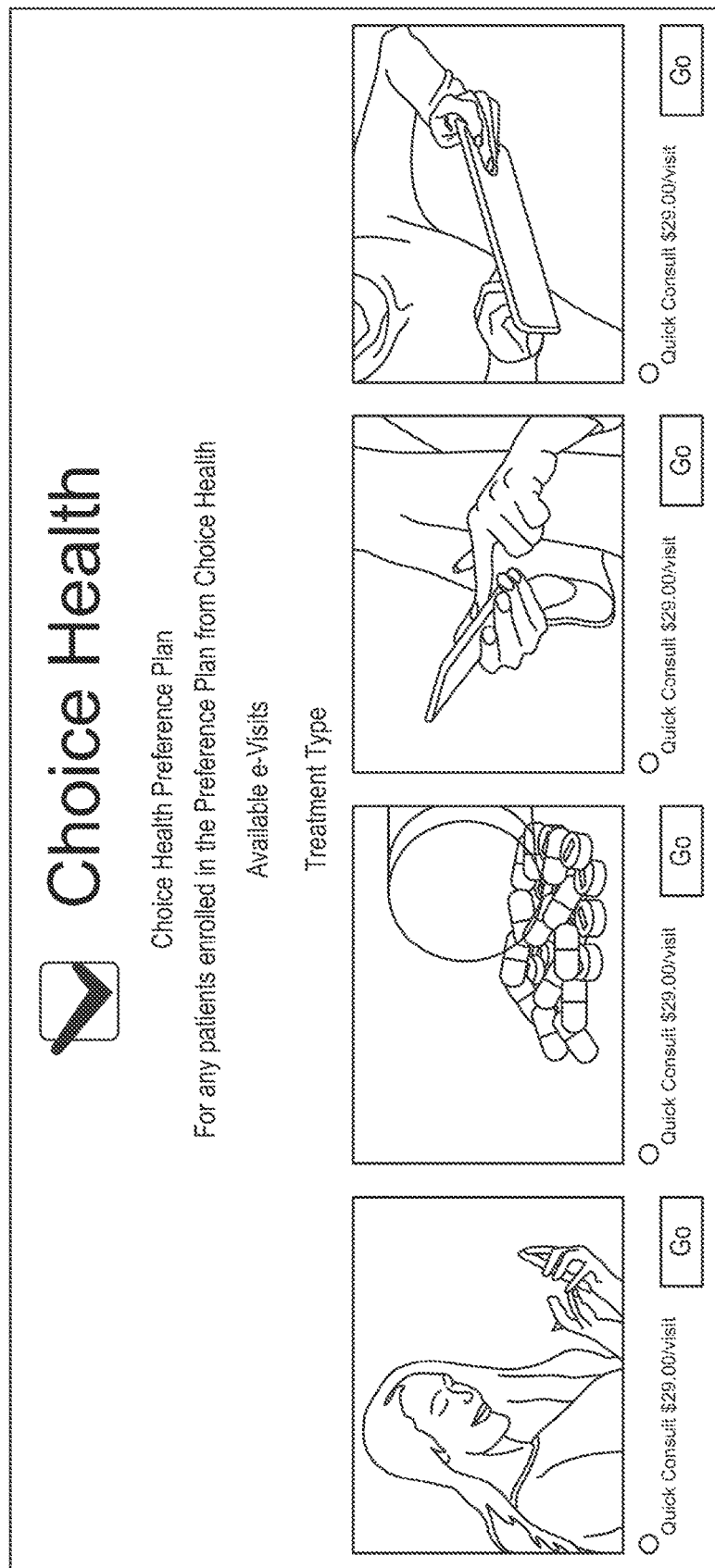
FIG. 6 illustrates a block diagram of a customized telemedicine portal automatically generated based on an available health plan, according to one embodiment.

FIG. 6 illustrates a block diagram 600 of a customized telemedicine portal automatically generated based on the Choice Health Preference Plan, according to various embodiments. As illustrated, the ATCG system may auto-generate unique clinics for providers that reflect individual health plans offered by the payer or business. In various embodiments, appointments may be uniformly managed by the provider from a dashboard, regardless of the number of payers or businesses for which the provider has a telemedicine clinic.

FIG. 7 illustrates a simplified screenshot 700 of a provider's unified electronic health record (EHR) combing information from all of his or her unique telemedicine clinics, according to one embodiment. The ATCG system may connect with a provider's existing scheduling platform or include a unifying scheduling portal to allow the provider to manage all scheduling for all of his or her telemedicine clinics from a single dashboard. Similarly, as illustrated, the provider's EHR, pharmacy management system, radiology information system, and/or the like may be integrated or interface with the ATCG system via an application programming interface (API).

FIG. 8 illustrates a simplified screenshot 800 of a provider's schedule integrated with information from all of the provider's unique telemedicine clinics, according to one embodiment. As illustrated, scheduled appointments may appear as a telehealth visit. In various embodiments, various additional information may be accessible, such as contracted rates, required co-pays, insurers, etc.

Figure 9:
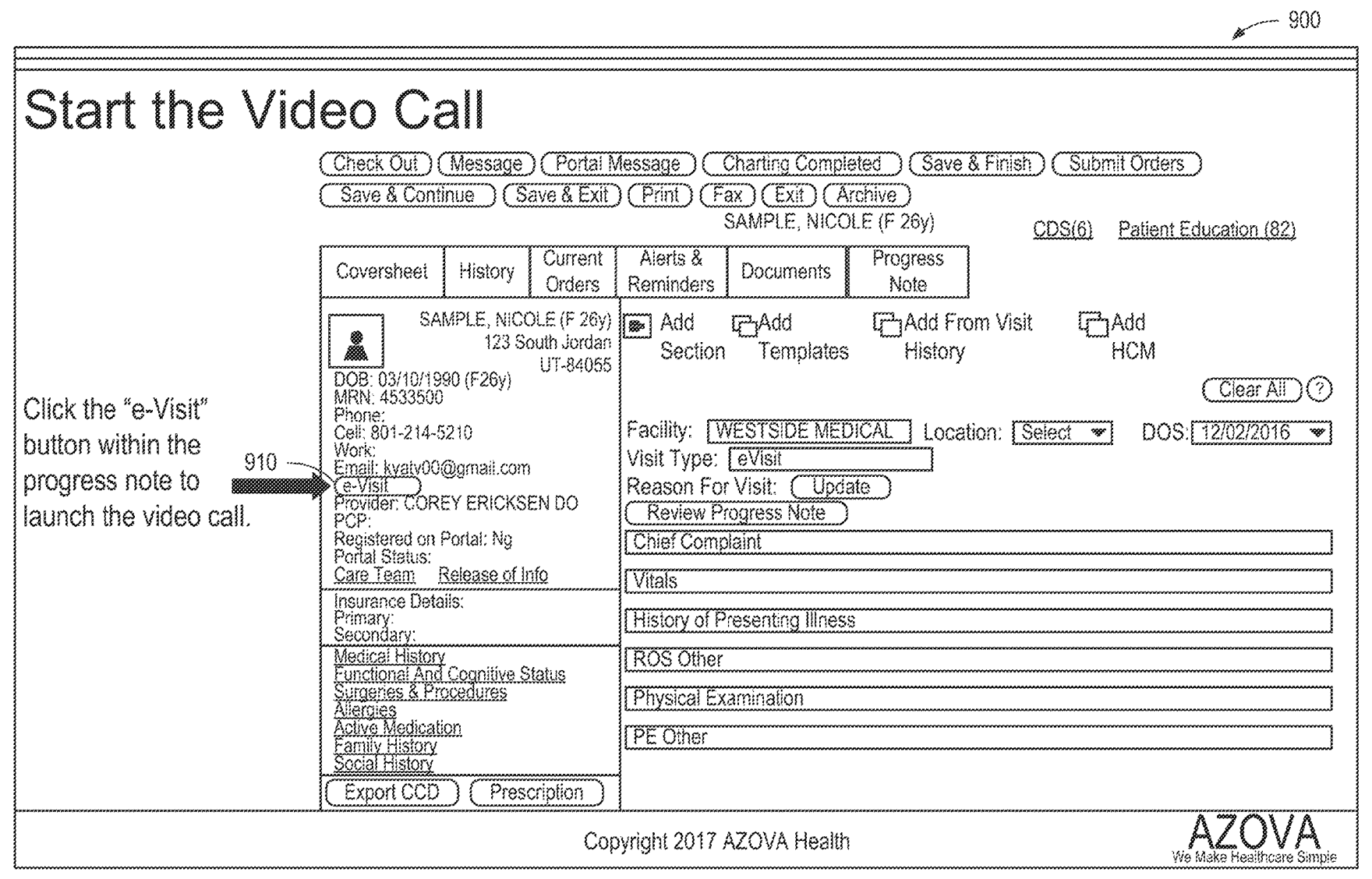

FIG. 9 illustrates an example portal 900 for initiating a telemedicine consultation, according to one embodiment. As illustrated, after providing personal information and/or identifying the patient, an "e-visit" button 910 may be selected to initiate the telemedicine session. In various embodiments, the telemedicine session may be initiated by the provider or by the patient and any of the various features and functionalities described in the '102 application may be available.

Figure 10:
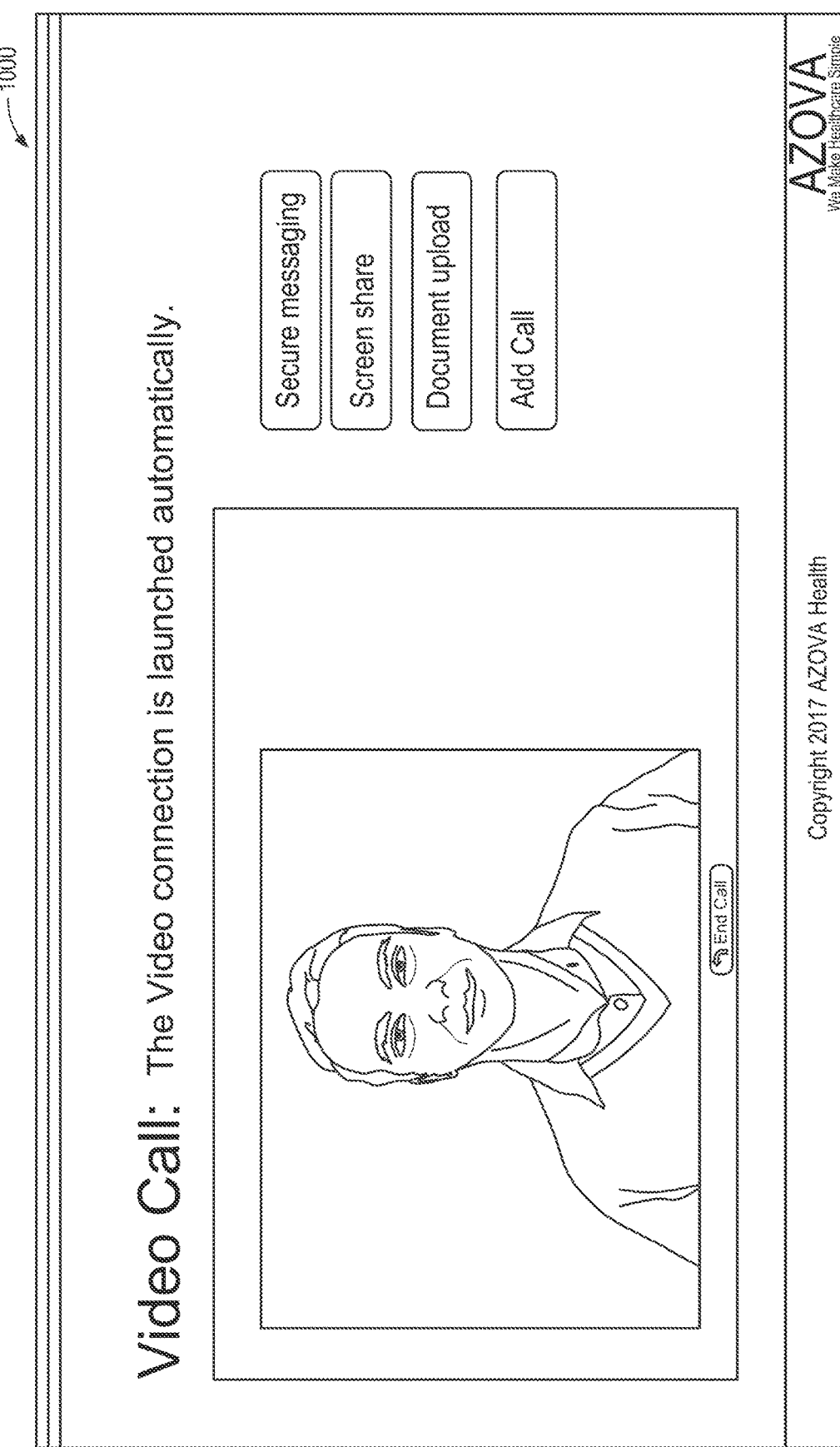
FIG. 10 illustrates an example of a telemedicine video consultation, according to one embodiment.

FIG. 10 illustrates an example of a telemedicine video consultation 1000, according to one embodiment. Examples and features available during a telemedicine video, such as document sharing, recording, etc. are detailed and described in the '102 application.

Figure 11:
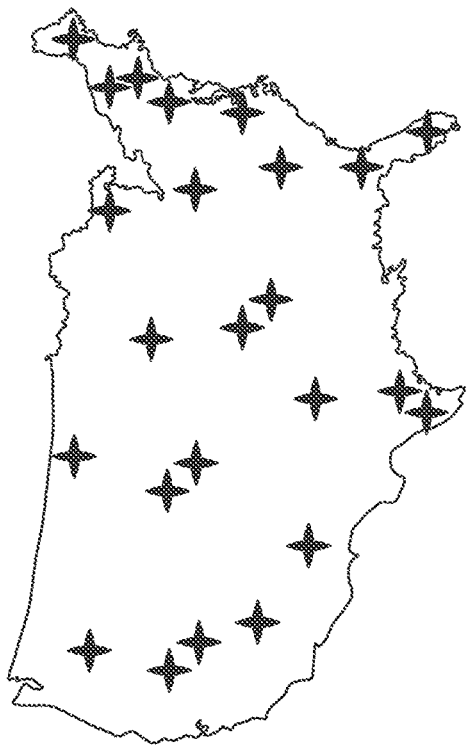
FIG. 11 illustrates an example of auto-generated clinics that become active when claimed by a provider.

FIG. 11 illustrates an example chart 1100 illustrating auto-generated clinics that become active when claimed and optionally customized by a provider. As previously described, in one embodiment or implementation, the ATCG system may auto-generate clinics for all providers within a geographic region. Before each of these clinics is actually available for patient use, providers may be claim and activate them. In one embodiment, it is free for the provider to activate or claim a clinic and it becomes immediately available for use. Each time the clinic is used, a surcharge or fee may be assessed to the patient, provider, or payer. Once a clinic has been claimed by a provider, a search page may be automatically populated for each payer or business associated with the provider who has claimed his/her online clinic. Patients can then access telehealth services from their own, established care providers.

FIG. 12 illustrates a user interface 1200 for a provider of any of a wide variety of professional service types to a register for the AZOVA™ platform.

Figure 13:
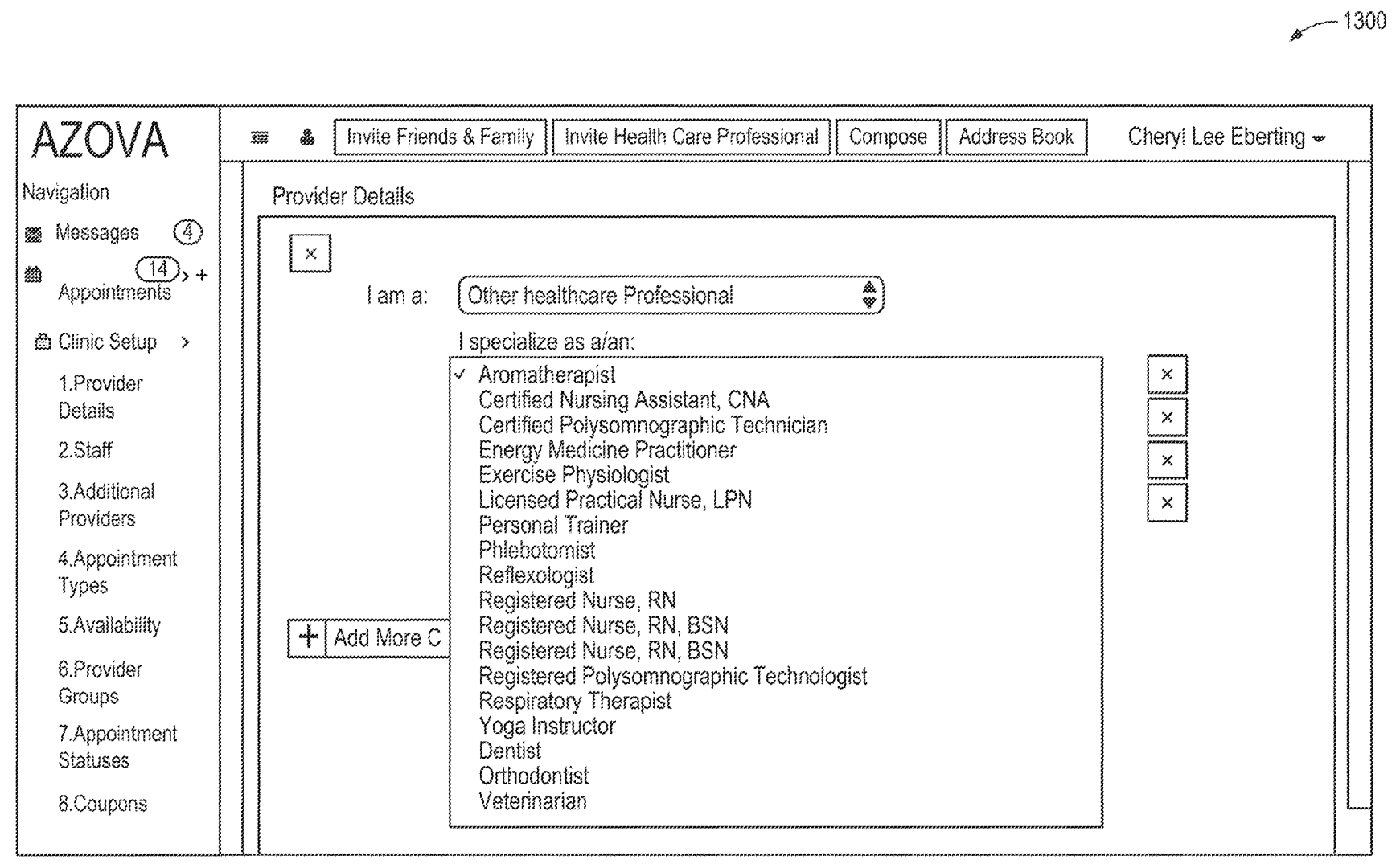

FIG. 13 illustrates another embodiment of a user interface 1300 for a provider of any of a wide variety of professional service types to a register for the AZOVA™ platform.

Figure 14:
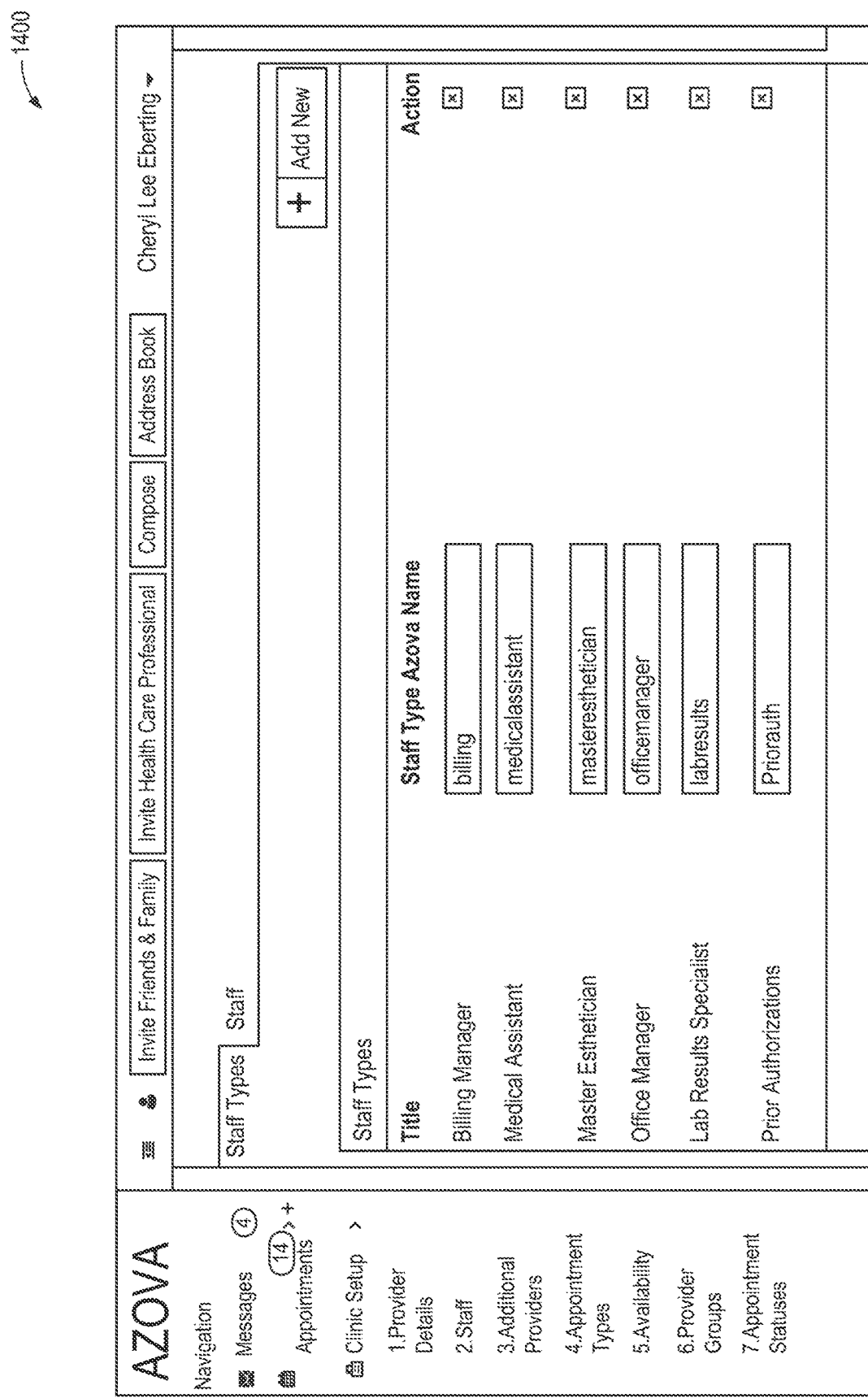
FIG. 14 illustrates a user interface for assigning individuals various roles with the AZOVA™ platform, according to various embodiments.

FIG. 14 illustrates a user interface 1400 for assigning individuals various roles with the AZOVA™ platform, according to various embodiments.

FIG. 15 illustrates a user interface 1500 for customizing and configuring appointment types, according to various embodiments.

FIG. 16A illustrates a user interface 1600 with various appointment types, prices, and options for customization.

FIG. 16B illustrates an extension 1650 of the user interface in FIG. 16A with additional options for customization of services, prices, and/or other terms that can be made available within a marketplace.

FIG. 17A illustrates a user interface 1700 for offering a concierge package provider service on the marketplace that offers unlimited in-office visits and face-to-face video consultations. As illustrated, various pricing options can be customized by via the user interface 1700.

FIG. 17B illustrates an extension 1750 of the user interface in FIG. 17A with additional customization options.

This disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element.

What is claimed is:

1. A distributed computing system for automatically generating telemedicine clinics, comprising:
   a provider identification system to identify a provider;
   a payer identification system to identify multiple payers associated with the provider; and
   a telemedicine clinic generation system to automatically create:
      a unique provider telemedicine clinic for each of the identified multiple payers such that the provider has multiple provider telemedicine clinics, wherein each provider telemedicine clinic allows patients associated with each respective payer to receive telemedicine healthcare services from the provider; and
      a unified telemedicine portal that can be accessed by the provider to provide telemedicine healthcare services to each patient via the provider telemedicine clinic of the payer associated with each respective patient.

2. The distributed computing system of claim 1, wherein the provider comprises one or more of: a doctor, a dentist, a pharmacist, and an ophthalmologist.

3. The distributed computing system of claim 1, wherein the provider comprises multiple healthcare practitioners collaborating in a healthcare facility.

4. The distributed computing system of claim 1, wherein each of the unique provider telemedicine clinics allows for patients to schedule appointments with the provider, and wherein the unified telemedicine portal unifies the scheduled appointments into a single schedule for the provider.

5. The distributed computing system of claim 1, wherein the provider identification system identifies providers based on a national provider identification (NPI) number.

6. The distributed computing system of claim 1, wherein at least one of the payers comprises a health insurance company, and wherein the patients associated with the health insurance company comprise employers.

7. The distributed computing system of claim 1, wherein at least one of the payers comprises a health insurance company, and wherein the patients associated with the health insurance company comprise individual insureds.

8. The distributed computing system of claim 1, wherein at least one of the payers comprises a non-insurance related business entity, and wherein the patients associated with the business entity comprise employees of the business entity.

9. The distributed computing system of claim 1, wherein telemedicine healthcare services comprise prescription consultations provided by a pharmacist.

10. The distributed computing system of claim 1, wherein the unified telemedicine portal comprises a patient user interface that enables the patient to view and selectively purchase healthcare products available for shipping to the patient that require a prescription from the provider.

11. The distributed computing system of claim 10, wherein the unified telemedicine portal further comprises a consultation module to initiate a telemedicine healthcare consultation between the patient and the provider.

12. The distributed computing system of claim 11, wherein the unified telemedicine portal further comprises a prescription generation module enabling the provider to generate a prescription in connection with a completed consultation to enable the patient to purchase at least one of the products that require a prescription.

13. A system, comprising:
a computing device to generate an electronic user interface to allow each of a plurality of providers to offer healthcare services via an online marketplace with customizable terms of service via provider telemedicine clinics, wherein each telemedicine clinic is associated with a unique insurance company and at least some providers offer healthcare services via multiple telemedicine clinics;
an electronic server interface to provide a business entity with access to a list of the healthcare services and associated terms of service offered by the plurality of providers;
an electronic user interface to allow the business entity to make an electronic selection of a subset of the plurality of providers for inclusion in an online marketplace;
a marketplace interface to allow the business entity to connect customers of the business with the selected subset of the plurality of providers; and
a telemedicine platform to allow the customers of the business entity to receive a telemedicine consultation from any one of the selected subset of the plurality of providers.

14. The system of claim 13, wherein the customizable terms of service include a customizable price structure for one or more offered healthcare services.

15. The system of claim 13, wherein the business entity selects the subset of the plurality of providers for inclusion in the online marketplace by setting threshold payment amounts for each of a plurality of healthcare services.

16. The system of claim 13, wherein the business entity comprises a health insurance company.

17. The system of claim 13, wherein the business entity comprises a manufacturing company.

18. A system, comprising:
a computing device to generate an electronic user interface to allow each of a plurality of providers to offer healthcare services via an online marketplace with customizable terms of service via provider telemedicine clinics;
an electronic server interface to provide a business entity with access to a list of the healthcare services and associated terms of service offered by each of the plurality of providers;
an electronic user interface to allow the business entity to make an electronic selection of a subset of the plurality of providers for inclusion in an online marketplace;
an electronic user interface to allow the business entity to make an electronic selection of a subset of healthcare services offered by each of the plurality of providers to be available to customers of the business entity, wherein the business entity excludes at least one healthcare service offered by at least one of the plurality of providers from availability to customers of the business entity;
a marketplace interface to allow the business entity to connect the customers of the business entity with the selected subset of the plurality of providers; and
a telemedicine platform to allow the customers of the business entity to receive a telemedicine consultation from the selected subset of the plurality of providers.

19. The system of claim 18, wherein the business entity comprises a health insurance company.

20. The system of claim 18, wherein the business entity comprises financial services company.

21. The system of claim 18, wherein at least some of the providers comprise pharmacists.

22. A distributed computing system to generate telemedicine clinics, comprising:
a provider identification system to:
identify a first set of providers associated with a first payer; and
identify a second set of providers associated with a second payer, wherein at least some providers are associated with the first payer and the second payer; and
a telemedicine clinic generation system to automatically create a unique provider telemedicine clinic for each provider,
wherein the provider telemedicine clinic for each provider associated with only the first payer is customized according to specifications of the first payer,
wherein the provider telemedicine clinic for each provider associated with only the second payer is customized according to specifications of the second payer, and
wherein the provider telemedicine clinic for each provider associated with both the first payer and the second payer is:
customized according to the specifications of the first payer when the provider is providing services to a patient associated with the first payer, and
customized according to the specifications of the second payer when the provider is providing services to a patient associated with the second payer.

23. The distributed computing system of claim 22, wherein each of the providers comprises one or more of: a doctor, a dentist, a pharmacist, and an ophthalmologist.

24. The distributed computing system of claim 22, wherein at least one of the payers comprises a health insurance company, and wherein the patients associated with the health insurance company comprise individual insureds.

25. The distributed computing system of claim 22, wherein at least one of the payers comprises a non-insurance related business entity, and wherein the patients associated with the business entity comprise employees of the business entity.

26. The distributed computing system of claim 22, wherein telemedicine healthcare services comprise prescription consultations provided by a pharmacist.

27. The distributed computing system of claim 22, wherein at least some of the provider telemedicine clinics comprise a telemedicine portal with a patient user interface that enables the patient to view and selectively purchase healthcare products available for shipping to the patient that require a prescription from the provider.

28. The distributed computing system of claim 27, wherein the telemedicine portal further comprises a consultation module to initiate a telemedicine healthcare consultation between the patient and the provider.

29. The distributed computing system of claim 28, wherein the telemedicine portal further comprises a prescription generation module enabling the provider to generate a prescription in connection with a completed consultation to enable the patient to purchase at least one of the products that require a prescription.

* * * * *